United States Patent
Goode et al.

(10) Patent No.: US 9,232,991 B2
(45) Date of Patent: Jan. 12, 2016

(54) APPARATUS AND METHOD FOR RETRIEVING AN IMPLANTED DEVICE FROM A BODY VESSEL

(71) Applicant: COOK MEDICAL TECHNOLOGIES LLC, Bloomington, IN (US)

(72) Inventors: Louis B. Goode, Cranberry Township, PA (US); Maureen A. Secilia, Kittanning, PA (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 338 days.

(21) Appl. No.: 13/770,227

(22) Filed: Feb. 19, 2013

(65) Prior Publication Data
US 2014/0236214 A1 Aug. 21, 2014

(51) Int. Cl.
*A61M 29/00* (2006.01)
*A61F 2/01* (2006.01)

(52) U.S. Cl.
CPC ............. *A61F 2/01* (2013.01); *A61F 2002/011* (2013.01)

(58) Field of Classification Search
CPC .............................. A61F 2/01; A61F 2002/011
See application file for complete search history.

(56) References Cited

U.S. PATENT DOCUMENTS

| | | | |
|---|---|---|---|
| 4,471,777 A * | 9/1984 | McCorkle, Jr. | ................ 606/129 |
| 6,699,260 B2 | 3/2004 | Dubrul et al. | |
| 6,712,826 B2 | 3/2004 | Lui | |
| 6,843,798 B2 * | 1/2005 | Kusleika et al. | .............. 606/200 |
| 7,118,539 B2 | 10/2006 | Vrba et al. | |
| 7,691,121 B2 | 4/2010 | Rosenbluth et al. | |
| 7,931,666 B2 | 4/2011 | Boyle et al. | |
| 2002/0072730 A1* | 6/2002 | McGill et al. | ................. 604/525 |
| 2012/0016407 A1 | 1/2012 | Sakai | |
| 2012/0022579 A1 | 1/2012 | Fulton | |
| 2012/0109180 A1 | 5/2012 | Shrivastava | |

\* cited by examiner

*Primary Examiner* — Gregory Anderson
(74) *Attorney, Agent, or Firm* — Brinks Gilson & Lione

(57) ABSTRACT

An apparatus for retrieving an implanted device from a body vessel includes a distal hub with an elongated, bendable distal tip and with a first marker visible through body tissue with at least one imaging method; a proximal hub with a central longitudinal channel therethrough, arranged proximal from the distal hub, and bearing a second marker. A stylet wire extends from the distal hub through the central longitudinal channel of the proximal hub to a proximal stylet wire end. A flexible, radially expandable interlocking arrangement extends from the distal hub to the proximal hub. An elongated positioning device extending proximally from the proximal hub to a proximal device end. The positioning device and the stylet wire may be configured to perform a longitudinal relative movement between proximal hub and the distal hub, and the interlocking arrangement expands radially when the proximal and distal hubs approach each other.

18 Claims, 2 Drawing Sheets

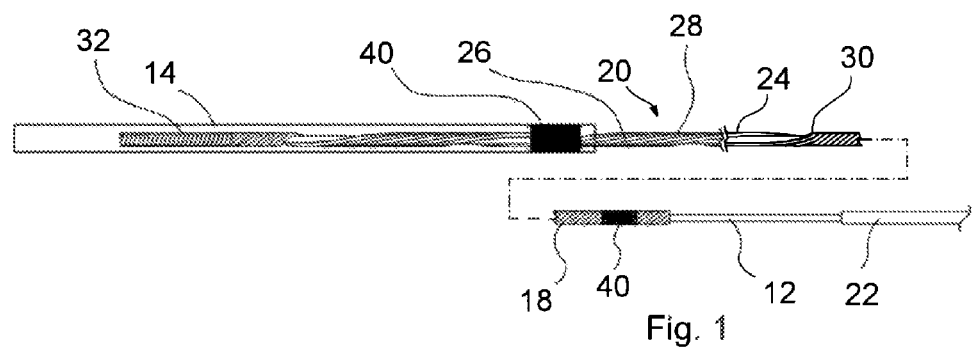
Fig. 1
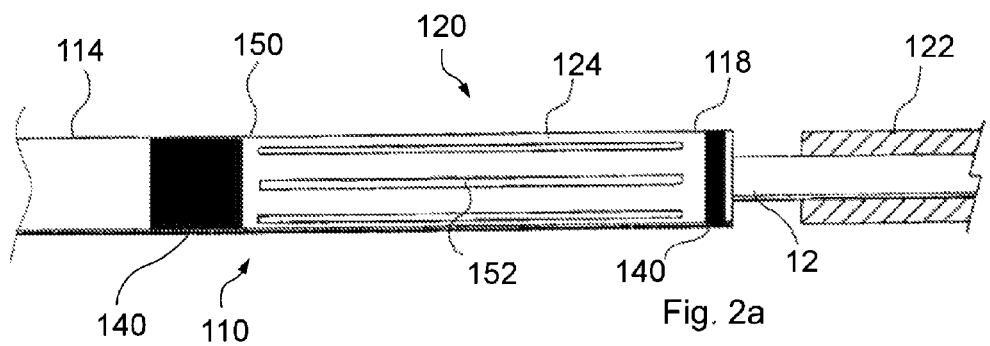
Fig. 2a
Fig. 2b
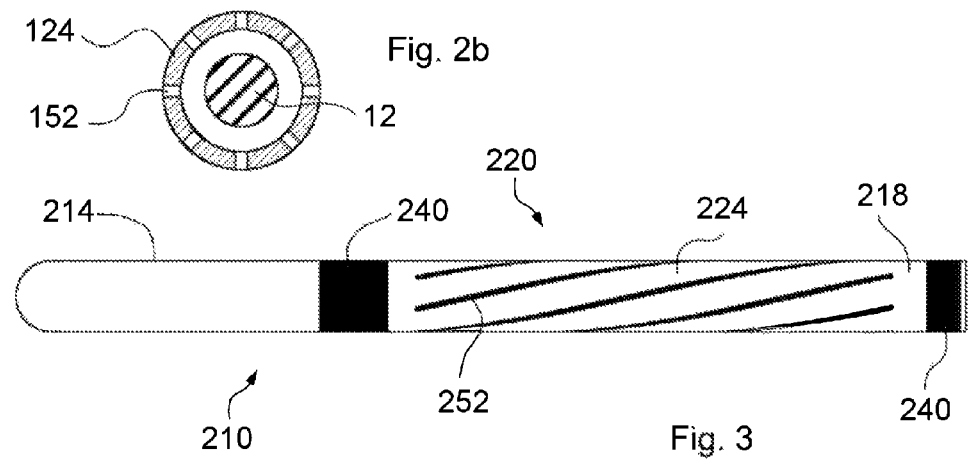
Fig. 3

APPARATUS AND METHOD FOR RETRIEVING AN IMPLANTED DEVICE FROM A BODY VESSEL

TECHNICAL FIELD

This invention relates to an apparatus for removing devices implanted in biological tissue. More particularly, the invention relates to an apparatus for removing a vena cava filter from a body vessel, especially a vena cava filter that may not be removable by grabbing a removal hook.

BACKGROUND

Filtering devices that are percutaneously placed in a vena cava have been available for many years. A need for filtering devices arises in trauma patients, orthopedic surgery patients, neurosurgery patients, or in patients having medical conditions requiring bed rest or non-movement. During such medical conditions, the need for filtering devices arises due to the likelihood of thrombosis in the peripheral vasculature of patients wherein thrombi break away from the vessel wall, risking downstream embolism or embolization. For example, depending on the size, such thrombi pose a serious risk of pulmonary embolism wherein blood dots migrate from the peripheral vasculature through the heart and into the lungs.

A filtering device can be deployed in the vena cava of a patient when, for example, anticoagulant therapy is contraindicated or has failed. Filters have been used or considered in preoperative patients and in patients predisposed to thrombosis which places the patient at risk for pulmonary embolism.

In certain situation, it is desirable to remove a vena cava filter from the patient body. After deployment of a filter in a patient, however, proliferating intimal cells begin to accumulate around the filter struts which contact the wall of the vessel. Additionally, filters may become off-centered or tilted with respect to the hub of the filter and the longitudinal axis of the vessel in which it has been inserted. As a result, the filter including the hub and the retrieval hook may engage the vessel wall along their lengths and potentially become endothelialized therein. Under such conditions, it is very difficult if not impossible to engage the retrieval hook in a known manner with a snare.

SUMMARY

It is an object of the present invention to provide an apparatus and a method that make it possible to retrieve a vena cava filter from a body vessel without engaging the retrieval hook of the vena cava filter.

According to a first aspect of the invention, a device for retrieving an implanted device from a body vessel is provided. The apparatus comprises a distal hub having an elongated, bendable distal tip and bearing a first marker visible through body tissue with at least one imaging method; a proximal hub with a central longitudinal channel therethrough, the proximal hub being arranged proximal from the distal hub and bearing a second marker visible through body tissue with the at least one imaging method; a stylet wire proximally extending from the distal hub through the central longitudinal channel of the proximal hub to a proximal stylet wire end; a flexible, radially expandable interlocking arrangement extending from the distal hub to the proximal hub; and an elongated positioning device extending proximally from the proximal hub to a proximal device end. The positioning device and the stylet wire may be configured to perform a longitudinal relative movement between proximal hub and the distal hub, and the interlocking arrangement may be configured to radially expand when the proximal and distal hubs approach each other.

According to another aspect of the invention, the interlocking arrangement may include a plurality of flexible elongated elements extending from the proximal hub to the distal hub. For example, the flexible elongated elements may be wires. According to a further aspect of the invention, the flexible elongated elements may be twisted around a portion of the stylet wire that extends between the proximal hub and the distal hub.

According to yet another aspect of the invention, the interlocking arrangement may include a plurality of bendable, generally flat strips extending from the proximal hub to the distal hub. The flat strips may be arranged circumferentially adjacent to each other and separated from each other by slits. Each of the flat strips may describe a helical curve around a portion of the stylet wire that extends between the proximal hub and the distal hub.

According to yet another aspect of the invention, the strips may be unitary with the distal hub.

According to another aspect of the invention the distal hub has a length of at least about 3 cm, preferably about 5 cm. Alternatively, the length of the distal hub may be about equal to a length of a vena cava filter.

According to a further aspect of the invention, the distal hub has a hub diameter and the interlocking arrangement has a passive state and an active state. In the passive state, the interlocking arrangement has a passive length and a passive diameter, and in the active state the interlocking arrangement has an active length and an active diameter. The passive diameter may be no greater than about the hub diameter, the active diameter may be greater than the hub diameter, and the passive length may be shorter than the active length. Further, the passive length of the interlocking arrangement may be smaller than the hub length of the distal hub. For example, the passive length may be between about 20 mm and about 40 mm, more particularly, between about 25 mm and about 35 mm.

According to yet another aspect of the invention, the passive length may be adjustable by inserting a subassembly into a tubular distal hub that radially restricts a distal first axial portion of the subassembly and allows an unrestricted radial expansion of a second axial portion proximal of the first axial portion, the second axial portion forming the radially expandable interlocking arrangement.

According to another aspect of the invention, the proximal hub may be formed by a coil of wires with axially gap-free windings.

According to yet another aspect of the invention, a method is provided for removing a generally cone-shaped, collapsible vena cava filter from a filter location inside a body vessel, wherein the vena cava filter has a filter hub at a hub side and a generally cone-shaped filter body extending from the filter hub toward a body side, the filter body having open spaces therethrough. The removal method comprises the steps of providing a catheter with a length about sufficient to extend from an operator to the filter location; providing a removal device with a distal hub having an elongated, bendable distal tip and bearing a first marker visible through body tissue with at least one imaging method; a proximal hub with a central longitudinal channel therethrough, the proximal hub being arranged proximal from the distal hub and bearing a second marker visible through body tissue with the at least one imaging method; and a flexible, radially expandable interlocking arrangement extending from the distal hub to the proximal hub; inserting the catheter into the body vessel from the hub side to a position, in which a distal end of the catheter resides proximally from the filter location; inserting the removal device through the catheter into the body vessel from the hub side; distally advancing the distal hub through one of the open spaces of the filter body to a position distal from the filter hub; further advancing the removal tool through the open space until the proximal hub is located distal from the filter hub inside the filter body; proximally moving the distal hub relative to the proximal hub so as to radially expand the interlocking arrangement; proximally retracting the removal tool while engaging at least one of the filter body and the filter hub; proximally displacing the vena cava filter into the distal end of the catheter; and removing the catheter.

Further details and advantages of the invention will become apparent from the following description of several embodiments of the invention shown in the accompanying drawings. The drawings are provided for purely illustrative purposes and are not intended to limit the scope of the invention.

BRIEF DESCRIPTION OF THE DRAWINGS

In the drawings,

FIG. 1 shows a first embodiment of a filter removal apparatus in accordance with the present invention;

FIG. 2a shows a partial view of a second embodiment of a filter removal apparatus according to the invention;

FIG. 2b shows a cross-section of the filter removal apparatus of FIG. 2a;

FIG. 3 shows a partial view of a third embodiment of a filter removal apparatus according to the invention.

DETAILED DESCRIPTION OF THE DRAWINGS

Figure 4A:
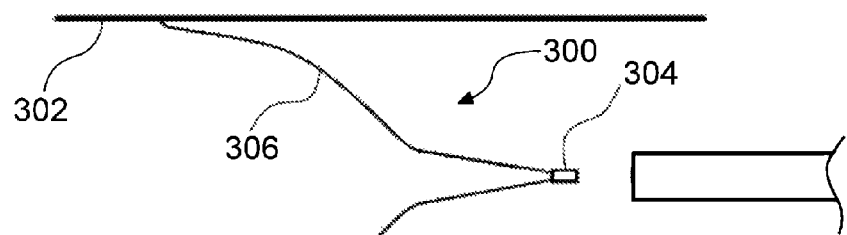
FIGS. 4a, 4b, 4c, and 4d show individual steps of a method for removing a vena cava filter from a body vessel by the example of the filter removal apparatus of FIG. 1.

The drawings are purely schematic illustrations of various aspects of the invention and are not necessarily to scale, unless expressly stated.

FIG. 1 depicts a first embodiment of a filter removal apparatus 10, that comprises a stylet 12, a distal hub 14 covering a distal end 16 of the stylet 12, a proximal hub 18 movably disposed around the stylet 12, and a radially expandable interlocking arrangement 20 extending from the distal hub 14 and distally attached to the proximal hub 18. An actuator portion 22, such as an elongate cannula is slidably disposed over the stylet 12 proximal from the interlocking arrangement 20.

The actuator portion 22 is shown at an axial distance from the proximal hub 18, but is preferably placed adjacent to the proximal hub during use as will be explained in connection with FIGS. 4a through 4d. The interlocking arrangement 20 has a plurality of expandable members 24 configured to deform plastically or elastically as the interlocking arrangement 20 is longitudinally compressed, at least some of the expandable members 24 eventually bowing outward.

The expandable members 24 provide a positive fixation inside the body of a vena cava filter, for example between struts, by filling up a space axially distal from a filter hub, which allows the stylet 12 retract the filter from the body vessel into which it has been implanted. This positive fixation with respect to a movement in the proximal direction allows the filter to be pulled proximally and to allow the struts of the filter body to withdraw from the walls of the body vessel. The filter removal apparatus 10 has a pull strength sufficient to provide the traction needed to free the filter, absent complicating factors such as extensive formation of scar tissue along the length of the lead. FIGS. 4a through 4d will illustrate further details of the filter removal process.

In the embodiment of FIG. 1, the expandable members 24 of the interlocking arrangement 20 are formed by a multifilar wire bundle 26 that comprises a series of adjacent wires 28 helically wrapped around the stylet 12. In the illustrative embodiment, the multifilar wire bundle 26 includes six individual expandable members 24 formed by the helically wound metal wires 28; however any practical number of wires 28 can be used. It has been found that using a multifilar wire bundle 26, rather than a single helically wound wire, allows for greater expansion. The shown arrangement results in a 0.015" outer diameter locking stylet that can expand to a sufficient diameter to engage and remove the vena cava filter. The term 'engage' as used within the portion of the specification describing the embodiments shown in FIGS. 1-4, is defined as a situation in which the expandable members 24 displace, shift, or otherwise intersperse with a filter body in a manner that forms a locking interaction or biting engagement.

One method of forming the multifilar wire bundle 26 is to helically wind the six individual wires 28 together over a pin with a diameter about equal to or slightly larger than that of the stylet 12 in the configuration that will ultimately be distally attached to the stylet 12. The individual wires 28 can be soldered together, if so desired, at their proximal end, which in that case, the stylet wire should be made of a material like titanium or nitinol or another material, to which the solder will not stick. Once helically wound, the multifilar wire bundle 26 is inserted over the stylet 12 as shown in FIG. 1.

The interlocking arrangement 20 comprising the multifilar wire bundle 26 of the illustrative embodiment is connected to both a relatively tightly wound distal portion 29 and the proximal hub 18. In the shown embodiment, the distal hub 14 fixates the tightly wound distal portion 29 of the multifilar wire bundle 26 that is affixed to the stylet 12 near the distal end 16 of the locking stylet 10 with a distal fixation joint 32 such as a solder joint, a crimped band, or some other well-known attachment of fixation means. Alternatively, the distal end of the interlocking arrangement may be fixated on the distal hub 14, which in turn may be fixed on the stylet 12.

In the illustrative embodiment of FIG. 1, the multifilar wire bundle 26 is wound with spaces between the windings of the expandable interlocking arrangement 20 to permit expansion during deployment by proximally pulling the distal hub 14 toward the proximal hub 18 with the stylet 12. While a radial expansion of the wires 28 can be achieved with wires 28 extending straight in a longitudinal direction between the proximal hub 18 and the distal hub 14, the twisted arrangement of the wires 28 further causes the wires 28 to intertwine with each other and to form a sturdy bunched structure 34 similar to a knot, as illustrated in FIG. 4c.

In FIG. 1, the proximal hub 18 is also formed by tightly wound proximal wire ends with a lumen of a diameter that allows a relative longitudinal movement between the proximal hub 18 and the stylet 12. In the area of the proximal hub 18, gaps between the individual wires 28 are generally minimal (e.g., about 0.0035") to nonexistent.

The distal hub 14 is formed by a flexible, elongated tip 36 in the shape of a unilaterally closed tube. The closed end 38 forms the distal end of the distal hub 14 and may be rounded for easier insertion into the body vessel. Both the proximal hub 18 and the distal hub 14 bear markers 40 visible through customary imaging methods, for example radiopaque markers for x-ray monitoring or echogenic markers for ultrasound monitoring. The marker 40 on the proximal hub is preferably arranged near the proximal end of the proximal hub to ensure, as will be described later, that the proximal hub 18 has been advanced past a filter hub. The marker 40 on the distal hub is preferably adjacent to or near the expandable arrangement 20 for monitoring the position of the distal hub 14 relative to the proximal hub 18. Because the distal hub 14 is longer than the proximal hub, the marker 40 disposed on the distal hub may be larger than the marker 40 on the proximal hub 18. It is, however, well within the scope of the present invention that the two markers 40 have the same size or that the markers 40 occupy the entire surface of the respective hub 14 or 18.

While in the shown example the individual wires 28 of the multifilar wire bundle 26 are aligned tightly together within the bundle 26, gaps between the wires 28 are well within the scope of the present invention. In the distal portion 29, gaps between the individual wires 28 are generally minimal (e.g., 0.0035") to nonexistent. The pitch, i.e. the longitudinal distance over which a given wire makes a 360° turn around the stylet 12, can vary for the interlocking arrangement 20, depending on a number of parameters (number of wires, wire diameter, etc.) and the range of expansion desired. In the illustrative embodiment, the expandable interlocking arrangement has a length of about 1.2" (3 cm) and includes a six-wire bundle 26 of about 0.004" stainless steel wire so that the multifilar wire bundle 26 measures about 0.024" in width. The length of the expandable interlocking arrangement 20 may vary depending on the desired application and may range between about 2 cm and about 4 cm, preferably between about 25 mm and about 35 mm.

Over the length of the interlocking arrangement 20, the wire bundle surrounds the stylet 12 about one or two times so that the pitch of the wires 28 lies in the range of about 1.5 cm to about 3 cm. These dimensions are merely illustrative and can be varied according to various structural parameters selected and the desired performance characteristics of the filter removal apparatus 10. At the proximal hub 18, a proximal fixation joint 30, such as a silver solder joint or other bonding means, may be included. At the proximal hub 18, only the individual wires 28 may be soldered together in the proximal fixation joint 30, leaving the interlocking arrangement 20 free to slide over the stylet 12 at that point. An optional ring, section of cannula, or other structure can be attached to the proximal hub 18 to provide a surface against which the actuator portion 22 may contact. Alternatively, the proximal hub 18 or the proximal end of the interlocking arrangement 20 may be attached to the actuator portion 22.

In the illustrative embodiment of FIG. 1, the stylet 12 comprises a 0.0075" 304 stainless steel spring tempered wire with a tensile strength of 382/455 ksi. The actuator portion 22 comprises a thin wall cannula, such as a 28 gauge hypodermic needle cannula. The actuator portion 22 extends approximately 60 cm to a distal handle (not shown) to which it is affixed. The wires 28 are, for example, 0.0035-0.004" annealed 304 stainless steel wires. The combination of a 0.0075" stylet 12 and 0.004" wires 28 yields a device having a 0.0155" outer diameter, but the invention is not limited to any of these dimensions.

As previously mentioned, the interlocking arrangement 20 is about 3 cm long. The distal hub 14 may have a length of up to about 5 cm, and the proximal hub may measure about 0.5 cm. The dimensions of the interlocking arrangement 20 can be quite variable. The length of the interlocking arrangement 20 being about 3 cm, however, allows for a sufficient radial expansion for removing a vena cava filter. Depending on the specific situation, a distal hub 14 of a shorter length may be used so that the interlocking arrangement 20 is longer because fewer windings are covered by the distal hub 14. For example, the distal hub may have a length within a range of about 3 cm to about 7 cm. The overall length of the locking stylet in FIG. 1 is approximately 140 cm.

As depicted in FIG. 1, proximal from the proximal hub 18, the actuator portion 22 provides support to axially compress and radially expand the expandable interlocking arrangement 20 by moving the distal hub 14 toward the proximal hub 18. The actuator portion 22 may even be formed integral with the proximal hub 18 adjacent the interlocking arrangement 20 or separate from the proximal hub 18. A braided tube of metal, plastic, or some other material may form the actuator portion 22. In each of these embodiments, handles on the proximal ends of the stylet 12 and the actuator portion 22 which are used to expand the expandable interlocking arrangement 20 are not shown in FIG. 1 and may be arranged in a known manner.

As previously noted, the configuration of the interlocking arrangement 20 is variable, largely depending on materials of its construction. It is preferred that the wires 28 be annealed; however, it is possible that only a selected portion of the interlocking arrangement 20, e.g. the expandable interlocking arrangement 20, be annealed, or it is possible to have different degrees of annealing across the length of the expandable portion. While the illustrative embodiment utilizes round wire, wires with alternate cross-sectional geometries (e.g., square, triangular, flattened, etc.) may be used to provide different properties for expanding and engaging the coils of the lead. Other features could be incorporated such as altering the surface properties of the wire by adding roughness or applying a polymeric coating that could possibly improving engagement with the coils. Yet another embodiment would be to include wires with different physical properties within a single multifilar wire bundle 26.

FIGS. 2a and 2b as well as FIG. 3 depict alternative expandable interlocking arrangements suitable for use in a filter removal apparatus similar to the embodiment shown in FIG. 1. In the embodiment of FIGS. 2a and 2b, a filter removal apparatus 110 comprises a tubular flexible element 150 that unitarily forms a distal hub 114, an expandable interlocking arrangement 120, and a proximal hub 118 as depicted in FIG. 2a. Expandable members 124 are formed as strips between axial slits 152 that extend in a substantially parallel manner along the length of the expandable interlocking arrangement 120. Markers 140 are applied to the distal hub and the proximal hub in analogy to the embodiment of FIG. 1.

The number of expandable members 124 correspond to the number of slits and is variable depending on the desired stiffness of the expandable members 124. The distal hub 114, which is not shown in its entire length, may be closed off at its distal end and is fastened to the distal end of a stylet 112 extending from the proximal side into the distal hub 114 in analogy to the removal apparatus of FIG. 1. The proximal hub 118, which is longitudinally movable relative to the stylet 112, may be separate from an actuator portion 122 as shown, or it may be connected to the actuator portion 122, in a unitarily manner or by attachment.

As illustrated in FIG. 2b, the stylet 112 extends centrally through the tubular flexible element without interfering with the expandable members 124. Due to the attachment of the stylet 112 to the distal hub 14, a proximal movement of the stylet relative to the proximal hub 118 and the actuator portion 112 causes the expandable members 124 to decrease their axial length and to increase the radial dimension.

FIG. 3 shows a variation of FIG. 2a. Like the embodiment of FIG. 2a, a filter removal apparatus 210 comprises a tubular flexible element 250 that unitarily forms a distal hub 214, an expandable interlocking arrangement 220, and a proximal hub 218. Expandable members 224 are formed between slits 252 that extend in a substantially parallel manner along the length of the expandable interlocking arrangement 220. In contrast to FIG. 2a, however, the slits 252 are slanted relative to the longitudinal direction so that they describe helical curves around a portion of the stylet. The slanted slits 252 have the effect that the individual expandable members 224 have a greater length than the expandable interlocking arrangement 220. Thus, a greater radial expansion can be achieved with the filter removal apparatus 210 of FIG. 3 compared to the filter removal apparatus 110 of FIG. 2a with an identical axial length of the expandable interlocking arrangements 120 and 220. Markers 240 are applied to the distal hub and the proximal hub in analogy to the embodiment of FIG. 1.

For obtaining the greatest possible radial expansion of the expandable members 224, the distal hub 214 moves proximally relative to the proximal hub 218 and also performs a relative rotational movement relative to the proximal hub in a direction that places the distal ends of the expandable members 224 in the same angular positions as the proximal ends of the expandable members 224. Both the proximal movement of the distal hub 214 and the rotation of the distal hub can be achieved by manipulating the stylet wire (not shown) for a proximal end of the filter removal device 210.

The number of expandable members 224 correspond to the number of slits 252 and is variable depending on the desired stiffness of the expandable members 224. The distal hub 214 is shown to be closed off at its distal end and is fastened to the distal end of the stylet (not shown) extending from the proximal side into the distal hub 214 in analogy to the removal apparatus of FIG. 1. As previously described, the proximal hub 218, which is longitudinally movable relative to the stylet, may be separate from an actuator portion, or it may be connected to the actuator portion, in a unitarily manner or by attachment.

FIGS. 4a through 4d illustrate a process of removing a vena cava filter from a body vessel. The steps of FIGS. 4a through 4d are illustrated by way of the embodiment shown in FIG. 1. The process, however applies in analogy to alternative embodiments of FIGS. 3a and 3b, and of FIG. 4.

In FIG. 4a, a vena cava filter 300 is schematically shown to be implanted in a body vessel 302. The vena cava filter 300 has a quasi-conical shape with a proximal filter hub 304 forming the apex of the quasi-conical shape and a plurality of struts 306 extending from the filter hub 304 outward in a distal direction to form the body of the quasi-cone.

Now referring to FIG. 4a, in order to retrieve the filter 300, an outer catheter 42 is placed proximally from the filter hub 304 in a generally known manner. The distal end 44 of the outer catheter 42 is placed close to the filter hub 304, for example about 0.5 cm to 2 cm away.

Figure 4B:
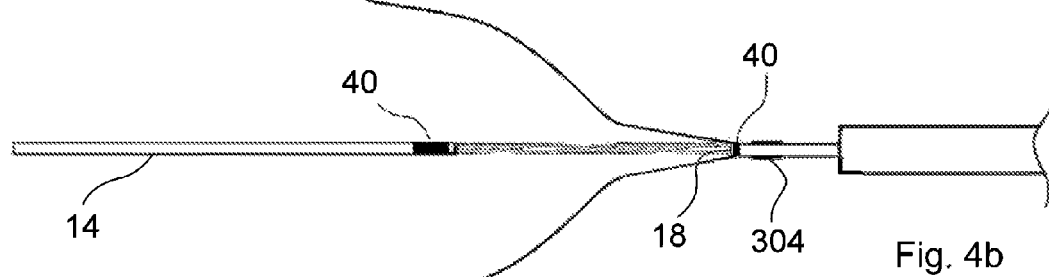
Figure 4C:
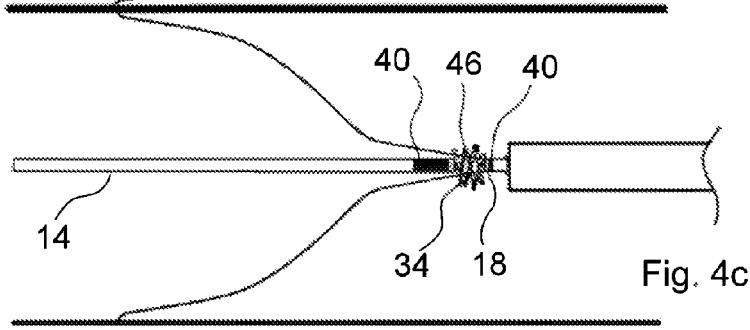

In a next step, as shown in FIG. 4b, the filter removal apparatus 10 is introduced into the outer catheter 42 and distally advanced. During this step, the interlocking arrangement 20 has a passive state, wherein in the passive state the interlocking arrangement 20 is passive, i.e. fully longitudinally extended without any radial expansion. In the passive state, the diameter of the expandable interlocking arrangement 20 is no greater than about the diameter of the distal hub 14 or the proximal hub 18. The interlocking arrangement 20 is advanced to a position relative to the filter 300 that places the proximal hub 18 distally from the filter hub 304. The proper position of the proximal hub 18 is verifiable by monitoring the position of the marker 40 on the proximal hub 18. In embodiments in which the actuator portion 22 is movable relative to the proximal hub 18, the actuator portion 22 is placed adjacent to the proximal hub 18 to prevent a proximal movement of the proximal hub 18 past the filter hub 304. The actuator portion 22 may optionally bear an additional marker for facilitating proper positioning. In all embodiments, the actuator portion 22 is then held in place for securing the position of the proximal hub 18 distal from the filter hub 304.

Subsequently, as illustrated in FIG. 4c, the stylet 12 is proximally withdrawn so as to cause a relative movement between the distal hub 14 and the proximal hub 18 so that the distal hub 14 approaches the proximal hub 18 so that the expandable interlocking arrangement occupies an active state. If the expandable members 24 are wound about the stylet in the passive state, the movement between the distal hub 14 and the proximal hub 18 may also involve a rotation that unwinds the expandable members 24. The expandable members 24 bulge outward and may additionally intertwine with each other, which may provide an increased stability of the active state. Expandable interlocking arrangements, such as the arrangements 20 and 220, with slanted or twisted expandable members 24 and 224 exhibit a greater tendency of intertwining members than those embodiments with axially straight expandable members 124, such as arrangement 120.

FIG. 4c shows the active state of the expandable interlocking arrangement 20, in which the wires 28 are bunched up into a radially expanded cluster 46. For verifying the proper position of the distal hub 14 to insure a proper formation of the cluster 46, the marker 40 on the distal hub 14 may be monitored, especially for its relative position with respect to marker 40 on the proximal hub 18. The resulting cluster 46 has a diameter that is greater than the diameters of the hubs 14, 18, and 304. Because the struts 306 extend distally from the filter hub 304, the distance between the proximal ends of the struts 306 is smaller than the diameter of the cluster 46. Accordingly, the cluster is confined between the struts distally from the filter hub 304. While the cluster 46 has a greater diameter than the hubs 14, 18, and 304, the cluster diameter is preferably small enough to be insertable into the distal end 44 of the catheter 42. This means that the cluster need not be smaller than the inner diameter of the catheter 42 if the respective expandable members 24 forming the cluster 46 are soft enough to be deflected while the filter removal apparatus 10 is retracted into the outer catheter 42.

Figure 4D:
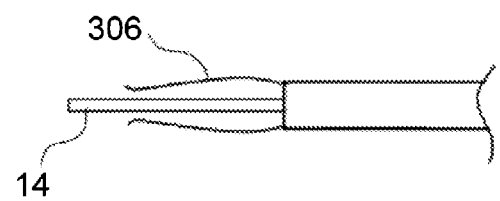

FIG. 4d shows a partially retracted filter removal apparatus that, due to the expanded interlocking arrangement 20 forming the cluster 46, takes along the vena cava filter. As the vena cava filter enters the outer catheter 42 with the filter hub entering the catheter before the struts, the struts are radially compressed so that the struts, like the filter hub, can be completely accommodated in the outer catheter (not shown).

After the entire filter removal apparatus 10 including the vena cava filter 300 has been accommodated inside the catheter 42, the filter removal apparatus 20 may be proximally removed from the catheter 42. Alternatively, the entire catheter may be withdrawn so that the filter removal apparatus 10 may be retrieved from the catheter 42 after the catheter has been withdrawn from the patient body.

Because the filter removal apparatus 10 and the described variations thereof do not need to engage with a filter retrieval hook, the filter removal apparatus 10 is suited even for vena cava filters that may reside in a tilted position, in which it is difficult to engage the retrieval hook, especially if the retrieval hook has been embedded in body tissue, for example due to overgrowth.

The foregoing description of various embodiments of the invention has been presented for purposes of illustration and description. It is not intended to be exhaustive or to limit the invention to the precise embodiments disclosed. Numerous modifications or variations are possible in light of the above teachings, and the properties of one embodiment may be modified with properties of another. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

What is claimed is:

1. An apparatus for retrieving an implanted device from a body vessel, comprising:
 a distal hub having an elongated, bendable distal tip and bearing a first marker visible through body tissue with at least one imaging method;
 a proximal hub with a central longitudinal channel therethrough, the proximal hub being arranged proximal from the distal hub and bearing a second marker visible through body tissue with the at least one imaging method;
 a stylet wire proximally extending from the distal hub through the central longitudinal channel of the proximal hub to a proximal stylet wire end;
 a flexible, radially expandable interlocking arrangement extending from the distal hub to the proximal hub and distally fixedly secured to the stylet wire; and
 an elongated positioning device extending proximally from the proximal hub to a proximal device end;
 the positioning device and the stylet wire being configured to perform a longitudinal relative movement between proximal hub and the distal hub, and the interlocking arrangement configured to radially expand when the proximal and distal hubs approach each other.

2. The apparatus of claim 1, wherein the expandable interlocking arrangement includes a plurality of flexible elongated elements extending from the proximal hub to the distal hub.

3. The apparatus of claim 2, wherein the flexible elongated elements are flexible wires.

4. The apparatus of claim 3, wherein the flexible wires are twisted around a portion of the stylet wire that extends between the proximal hub and the distal hub.

5. The apparatus of claim 1, wherein the interlocking arrangement includes a plurality of bendable, generally flat strips extending from the proximal hub to the distal hub, the flat strips being arranged circumferentially adjacent to each other and separated from each other by slits.

6. The device of claim 5, wherein each of the flat strips describes a helical curve around a portion of the stylet wire that extends between the proximal hub and the distal hub.

7. The apparatus of claim 5, wherein the strips are unitary with the distal hub.

8. The apparatus of claim 1 wherein the distal hub has a length of at least about 3 cm.

9. The apparatus of claim 8, wherein the distal hub has a length of about 5 cm.

10. The apparatus of claim 8, wherein the length of the distal hub is about equal to a length of a vena cava filter.

11. The apparatus of claim 1, wherein the distal hub has a hub diameter and the interlocking arrangement has a passive state and an active state, wherein in the passive state the interlocking arrangement has a passive length and a passive diameter, and wherein in the active state the interlocking arrangement has an active length and an active diameter, the passive diameter being no greater than about the hub diameter, the active diameter being greater than the hub diameter, and the passive length being shorter than the active length.

12. The apparatus of claim 11, wherein the distal hub has a hub length, the passive length of the interlocking arrangement being smaller than the hub length.

13. The apparatus of claim 11, wherein the passive length is between about 2 cm and about 4 cm.

14. The apparatus of claim 12, wherein the passive length is between about 25 mm and about 35 mm.

15. The apparatus of claim 11, wherein passive length is adjustable by inserting a subassembly into the distal hub, the distal hub radially restricting a distal first axial portion of the subassembly and allowing an unrestricted radial expansion of a second axial portion proximal of the first axial portion, the second axial portion forming the radially expandable interlocking arrangement.

16. The apparatus of claim 1, wherein the proximal hub is formed by a coil of wires with axially gap-free windings.

17. A method of removing a generally cone-shaped, collapsible vena cava filter from a filter location inside a body vessel, wherein the vena cava filter has a filter hub at a hub side and a generally cone-shaped filter body extending from the filter hub toward a body side, the filter body having open spaces therethrough, and wherein a removal apparatus includes a distal hub having an elongated, bendable distal tip and bearing a first marker visible through body tissue with at least one imaging method; a proximal hub with a central longitudinal channel therethrough, the proximal hub being arranged proximal from the distal hub and bearing a second marker visible through body tissue with the at least one imaging method; and a flexible, radially expandable interlocking arrangement extending from the distal hub to the proximal hub; the method comprising the following steps:
 inserting a catheter into the body vessel from the hub side to a position, in which a distal end of the catheter resides proximally from the filter location;
 inserting the removal device through the catheter into the body vessel from the hub side;
 distally advancing the distal hub through one of the open spaces of the filter body to a position distal from the filter hub;
 further advancing the removal tool through the open space until the proximal hub is located distal from the filter hub inside the filter body;
 proximally moving the distal hub relative to the proximal hub so as to radially expand the interlocking arrangement;
 proximally retracting the removal tool while engaging at least one of the filter body and the filter hub;
 proximally displacing the vena cava filter into the distal end of the catheter; and
 removing the catheter.

18. The method of claim 17, wherein the radially expandable interlocking arrangement has flexible strips or wires twisted around a stylet wire, the method comprising the further step of rotating the distal hub and the proximal hub relative to each other in a direction of untwisting the flexible strips or wires while the proximal hub is located distal from the filter hub.

* * * * *